United States Patent
Lawyer et al.

(10) Patent No.: US 12,099,047 B1
(45) Date of Patent: Sep. 24, 2024

(54) SENSORS, SYSTEM AND METHODS FOR MONITORING AND ADJUSTING CONDITIONS OF AN AQUARIUM

(71) Applicant: EcoTech Marine, LLC, Allentown, PA (US)

(72) Inventors: Justin Lawyer, Bethlehem, PA (US); Timothy Marks, Northampton, PA (US); Patrick Clasen, Allentown, PA (US); Christian Clough, Bethlehem, PA (US); Mark Lindenmoyer, Coopersburg, PA (US)

(73) Assignee: EcoTech, LLC, Bethlehem, PA (US)

( * ) Notice: Subject to any disclaimer, the term of this patent is extended or adjusted under 35 U.S.C. 154(b) by 761 days.

(21) Appl. No.: 17/172,590

(22) Filed: Feb. 10, 2021

Related U.S. Application Data

(60) Provisional application No. 62/972,321, filed on Feb. 10, 2020.

(51) Int. Cl.
 *G01N 33/18* (2006.01)
 *G01F 23/00* (2022.01)
 (Continued)

(52) U.S. Cl.
 CPC ............. *G01N 33/18* (2013.01); *G01F 23/00* (2013.01); *G01K 13/026* (2021.01); *H04Q 9/00* (2013.01); *H04Q 2209/40* (2013.01)

(58) Field of Classification Search
 CPC ............. G01N 33/0006; G01N 21/274; G01N 27/4165; G01N 35/00693; G01N 27/4163; G01N 27/3274; G01N 33/48771; G01N 21/3504; G01N 33/497; G01N 30/8665; G01N 2291/0256; G01N 33/0031; G01N 33/2823; G01N 15/1012; G01N 21/278; G01N 35/00594; G01N 27/126; G01N 33/005; G01N 27/16; G01N 33/0026; G01N 33/007; G01N 33/48; G01N 33/49; G01N 21/05; G01N 29/024; G01N 33/0047; G01N 33/28; G01N 33/2888; G01N 13/00; G01N 2030/626; G01N 21/0303; G01N 2291/02818; G01N 29/022; G01N 29/036; G01N 30/8668; G01N 33/96; G01N 35/08; G01N 9/36; G01N 1/4077; G01N 15/0656; G01N 2030/047; G01N 21/645; G01N 21/7703; G01N 21/783; G01N 21/8483;
 (Continued)

(56) References Cited

U.S. PATENT DOCUMENTS 8,266,465 B2 * 9/2012 Hardman .............. G06F 1/3209
340/447

FOREIGN PATENT DOCUMENTS

CN 108646636 A * 10/2018 ........... G05B 19/042
CN 208421588 U * 1/2019 ........... G05B 19/042

* cited by examiner

*Primary Examiner* — Andre J Allen
(74) *Attorney, Agent, or Firm* — Calderon, Safran & Wright P.C.

(57) ABSTRACT

The invention relates to sensor assemblies and systems for monitoring the condition inside a container, such as an aquarium, vivarium, or terrarium. The sensor assemblies operate in a manner to conserve battery life and minimize power usage. The system includes one or more sensor assemblies, one or more output device associated with the one or more sensor assemblies, a user interface, and a main system. The components of the system communicate with each other wirelessly and include hardware and software platforms for their operation.

19 Claims, 12 Drawing Sheets

(51) Int. Cl.
*G01K 13/00* (2021.01)
*G01K 13/02* (2021.01)
*H04Q 9/00* (2006.01)

(58) Field of Classification Search
CPC .............. G01N 30/96; G01N 33/0011; G01N 35/1016; G01N 1/2273; G01N 1/24; G01N 13/04; G01N 15/0255; G01N 2001/2223; G01N 2021/6441; G01N 2030/027; G01N 2035/00158; G01N 21/648; G01N 2291/0423; G01N 27/4077; G01N 33/0009; G01N 33/18; G01N 33/2852; G01N 33/54373; G01N 35/00712; G01N 35/1095; G01N 1/2202; G01N 1/405; G01N 15/1456; G01N 15/1459; G01N 2009/006; G01N 2035/00108; G01N 2291/0215; G01N 2291/02809; G01N 2291/02836; G01N 2291/02881; G01N 25/18; G01N 27/04; G01N 27/125; G01N 27/127; G01N 27/283; G01N 27/4045; G01N 29/222; G01N 29/326; G01N 30/02; G01N 30/20; G01N 30/88; G01N 33/004; G01N 33/487; G01N 33/492; G01N 33/4972; G01N 33/84; G01N 35/00732; G01N 9/002; G01N 1/34; G01N 1/40; G01N 11/16; G01N 15/06; G01N 15/065; G01N 2001/4016; G01N 2001/4066; G01N 2011/0013; G01N 2015/1477; G01N 2015/1486; G01N 2021/7786; G01N 2030/025; G01N 2035/00247; G01N 21/6486; G01N 22/00; G01N 2291/02433; G01N 2291/02466; G01N 2291/0255; G01N 27/026; G01N 27/12; G01N 27/223; G01N 27/3271; G01N 27/4175; G01N 27/44721; G01N 27/44791; G01N 30/32; G01N 30/6095; G01N 31/12; G01N 31/16; G01N 31/22; G01N 33/00; G01N 33/0036; G01N 33/2847; G01N 33/48714; G01N 33/5302; G01N 33/66; G01N 35/025; G01N 11/14; G01N 15/1031; G01N 2015/1415; G01N 2021/6432; G01N 2030/085; G01N 2030/8804; G01N 2030/965; G01N 2035/00326; G01N 21/253; G01N 21/33; G01N 21/6408; G01N 22/04; G01N 2201/0221; G01N 2201/12746; G01N 27/06; G01N 27/07; G01N 27/327; G01N 27/38; G01N 30/86; G01N 33/1846; G01N 35/00029; G01N 9/00; G01N 1/2208; G01N 1/2214; G01N 1/2258; G01N 11/00; G01N 15/02; G01N 15/0272; G01N 2001/2893; G01N 2011/0006; G01N 2011/002; G01N 2013/003; G01N 2021/3144; G01N 2021/3595; G01N 2021/6439; G01N 2021/772; G01N 2021/7773; G01N 2030/042; G01N 2030/204; G01N 2030/847; G01N 2035/00554; G01N 2035/00752; G01N 2035/00772; G01N 2035/1032; G01N 21/359; G01N 21/4133; G01N 21/534; G01N 21/554; G01N 21/61; G01N 21/6428; G01N 21/643; G01N 21/80; G01N 21/85; G01N 21/8507; G01N 2291/015; G01N 2291/0257; G01N 2291/0426; G01N 27/122; G01N 27/18; G01N 27/221; G01N 27/403; G01N 27/4145; G01N 27/4148; G01N 27/44743; G01N 29/032; G01N 29/42; G01N 29/46; G01N 30/62; G01N 33/0013; G01N 33/0029; G01N 33/0034; G01N 33/0045; G01N 33/1806; G01N 33/30; G01N 33/4875; G01N 33/48785; G01N 33/6848; G01N 35/00; G01N 35/00663; G01N 35/10; G01N 1/14; G01N 1/28; G01N 15/0205; G01N 15/05; G01N 15/1404; G01N 15/1425; G01N 15/1427; G01N 15/1429; G01N 2015/025; G01N 2015/1018; G01N 2015/1438; G01N 2030/201; G01N 2030/202; G01N 2030/8881; G01N 2035/00702; G01N 21/276; G01N 21/31; G01N 21/552; G01N 21/6452; G01N 21/658; G01N 21/77; G01N 21/78; G01N 2291/0212; G01N 2291/048; G01N 2291/102; G01N 27/407; G01N 27/622; G01N 27/626; G01N 27/70; G01N 29/323; G01N 29/4472; G01N 30/24; G01N 30/34; G01N 30/8658; G01N 33/0004; G01N 33/0049; G01N 33/0063; G01N 33/0065; G01N 33/0075; G01N 33/343; G01N 33/48792; G01N 35/00623; G01N 35/00871; G01N 35/0095; G01N 35/1009; G01N 7/10; G01N 1/10; G01N 1/2035; G01N 1/22; G01N 1/2294; G01N 1/36; G01N 1/38; G01N 1/4005; G01N 1/4022; G01N 1/4055; G01N 11/08; G01N 15/042; G01N 15/0618; G01N 15/08; G01N 15/0826; G01N 15/12; G01N 15/1209; G01N 15/1227; G01N 15/1434; G01N 2001/021; G01N 2001/024; G01N 2001/028; G01N 2001/1093; G01N 2001/2241; G01N 2001/225; G01N 2001/2261; G01N 2001/227; G01N 2001/4027; G01N 2011/008; G01N 2015/0088; G01N 2015/0261; G01N 2015/0288; G01N 2015/0693; G01N 2015/0846; G01N 2015/0873; G01N 2015/1025; G01N 2015/1087; G01N 2015/1409; G01N 2015/1493; G01N 2021/0346; G01N 2021/054; G01N 2021/1793; G01N 2021/3137; G01N 2021/478; G01N 2021/6482; G01N 2021/8521; G01N 2030/009; G01N 2030/062; G01N 2030/121; G01N 2030/128; G01N 2030/205; G01N 2030/3007; G01N 2030/3076; G01N 2030/3084; G01N 2030/8488; G01N 2030/8822; G01N 2030/8831; G01N 2030/8886; G01N 2035/00306; G01N 2035/00495; G01N 2035/00762; G01N 2035/009; G01N 2035/042; G01N 2035/1025; G01N 2035/1039; G01N 2035/1041; G01N 2035/1086; G01N 21/00; G01N 21/03; G01N 21/07; G01N 21/13; G01N 21/293; G01N 21/3554; G01N 21/3563; G01N 21/3577; G01N 21/53; G01N 21/553; G01N 21/59; G01N 21/67; G01N 21/73; G01N 21/76; G01N 21/7743; G01N 21/79; G01N 21/958;
G01N 2201/0245; G01N 2201/12; G01N
2201/127; G01N 2201/12753; G01N
2201/12769; G01N 2203/0094; G01N
2291/014; G01N 2291/0224; G01N
2291/0226; G01N 2291/024; G01N
2291/02491; G01N 2291/02827; G01N
2291/02872; G01N 2291/044; G01N
2291/106; G01N 23/09; G01N 2496/10;
G01N 2496/70; G01N 25/00; G01N
25/30; G01N 25/36; G01N 2600/00;
G01N 27/041; G01N 27/048; G01N
27/123; G01N 27/124; G01N 27/128;
G01N 27/226; G01N 27/26; G01N 27/28;
G01N 27/302; G01N 27/3272; G01N
27/333; G01N 27/3335; G01N 27/4035;
G01N 27/4065; G01N 27/4067; G01N
27/4071; G01N 27/4074; G01N 27/414;
G01N 27/4141; G01N 27/4146; G01N
27/416; G01N 27/4166; G01N 27/4167;
G01N 27/447; G01N 27/44717; G01N
27/44752; G01N 27/44782; G01N
2800/52; G01N 29/30; G01N 29/4436;
G01N 29/4481; G01N 30/00; G01N
30/12; G01N 30/30; G01N 30/462; G01N
30/463; G01N 30/466; G01N 30/468;
G01N 30/7266; G01N 30/74; G01N
30/82; G01N 30/84; G01N 30/8631;
G01N 30/8672; G01N 30/8675; G01N
31/00; G01N 31/005; G01N 31/162;
G01N 33/0001; G01N 33/0018; G01N
33/0022; G01N 33/0027; G01N 33/0037;
G01N 33/0059; G01N 33/03; G01N
33/15; G01N 33/1826; G01N 33/1866;
G01N 33/2025; G01N 33/22; G01N
33/24; G01N 33/246; G01N 33/2858;
G01N 33/32; G01N 33/48721; G01N
33/48728; G01N 33/4905; G01N
33/4915; G01N 33/493; G01N 33/52;
G01N 33/53; G01N 33/543; G01N
33/54326; G01N 33/551; G01N
33/56972; G01N 33/582; G01N 33/60;
G01N 33/6842; G01N 33/721; G01N
33/723; G01N 33/726; G01N 33/9493;
G01N 35/00069; G01N 35/026; G01N
35/028; G01N 35/085; G01N 5/045;
G01N 7/00; G01N 7/02; G01N 7/04;
G01N 9/04; G01N 9/10; G01N 9/28;
G01N 1/00; G01N 1/18; G01N 1/2247;
G01N 1/286; G01N 1/44; G01N
2001/002; G01N 2001/1436; G01N
2001/185; G01N 2001/2267; G01N
2001/2873; G01N 2009/008; G01N
2015/0046; G01N 2021/058; G01N
2021/1772; G01N 2021/3129; G01N
2021/3155; G01N 2021/3513; G01N
2021/7716; G01N 2021/7723; G01N
2021/7763; G01N 2021/7793; G01N
2021/8494; G01N 2030/326; G01N
2030/328; G01N 2030/347; G01N
2030/385; G01N 2030/889; G01N
2033/0019; G01N 2035/00673; G01N
2035/00811; G01N 2035/00831; G01N
2035/00851; G01N 2035/00891; G01N
2035/0097; G01N 2035/0429; G01N
2035/0441; G01N 2035/1044; G01N
21/01; G01N 21/25; G01N 21/3103;
G01N 21/314; G01N 21/474; G01N
21/75; G01N 2201/024; G01N
2201/0407; G01N 2201/0612; G01N
2201/0662; G01N 2201/068; G01N
2201/101; G01N 2201/103; G01N
2201/12723; G01N 2201/129; G01N
2203/021; G01N 2203/0222; G01N
2430/00; G01N 27/00; G01N 27/304;
G01N 27/308; G01N 27/41; G01N 27/87;
G01N 27/9006; G01N 27/904; G01N
2800/162; G01N 2800/24; G01N 3/567;
G01N 30/22; G01N 30/36; G01N 30/38;
G01N 31/225; G01N 33/0008; G01N
33/0014; G01N 33/0032; G01N 33/0057;
G01N 33/5438; G01N 33/6818; G01N
35/00603; G01N 35/04; G01K 15/00;
G01K 15/007; G01K 13/02; G01K 3/005;
G01K 3/10; G01K 1/045; G01F 25/0092;
G01F 11/28; G01F 23/265; G01F 23/266;
G01F 1/8409; G01F 1/849; G01F 1/00;
G01F 1/8413; G01F 1/8418; G01F
1/8436; G01F 1/8477; G01F 11/32; G01F
11/38; G01F 15/00; G01F 15/02; G01F
15/024; G01F 23/263; G01F 23/2961;
G01F 23/2962; G01F 23/2965; G01F
25/10; G01F 1/74; G01F 25/20
USPC .................................................. 73/1.02
See application file for complete search history.

US 12,099,047 B1

SENSORS, SYSTEM AND METHODS FOR MONITORING AND ADJUSTING CONDITIONS OF AN AQUARIUM

REFERENCE TO RELATED APPLICATION AND PRIORITY CLAIM

This application claims the priority of U.S. Provisional Patent Application No. 62/972,321, filed Feb. 10, 2020, which is incorporated herein by reference.

FIELD OF THE INVENTION

The present invention relates to sensor assemblies, systems and methods for monitoring and adjusting conditions inside a container, such as an aquarium, vivarium, or terrarium. The sensor assemblies operate in a manner to conserve battery life and minimize power usage.

BACKGROUND

In order to properly care for fish, other aquatic organisms, or animals contained within an aquarium, vivarium, terrarium or like habitat, environment conditions therein must be adequately controlled to ensure survival. The environmental conditions include temperature, pH, water level, humidity, oxygen level, etc. In some cases, a slight change in the environmental conditions can result in a loss of the organisms or animals, which can be costly in terms of time and money. Therefore, there remains a need for a system to monitor and control the environmental conditions within the aquarium, vivarium, terrarium or like habitat to maximize survival of the organisms or animals therein.

BRIEF DESCRIPTION OF THE DRAWINGS

The following detailed description of the invention will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings.

SUMMARY OF THE INVENTION

The present invention relates to sensors and systems useful to control and monitor one or more environmental conditions in connection with an aquarium, vivarium, terrarium or like habitat. The embodiments of this invention provide a system by which a user may efficiently and effectively maintain and monitor a multitude of environmental conditions within an aquarium, vivarium, terrarium or like habitat.

Accordingly, an aspect of the present invention provides sensor assemblies for monitoring identified environmental conditions. The sensor assemblies are configured to measure conditions within the aquarium, vivarium, terrarium or like habitat, such as temperature, conductivity, pH, oxygen reduction potential, liquid level, turbidity, humidity, or combinations thereof. Each sensor assembly includes a housing containing a sensor, a transmitter electronically connected to the sensor for transmitting and/or receiving data, and a power source providing power to the sensor and/or the transmitter. The sensor assembly is configured to be magnetically positioned onto a wall of the aquarium, vivarium, terrarium or like habitat.

Another aspect of the present invention relates to a system for monitoring and controlling environmental conditions within the aquarium, vivarium, terrarium or like habitat. The system includes one or more sensor assemblies, one or more output devices associated with the one or more sensor assemblies, a user interface, and a main control system. The components of the monitoring system communicate with each other wirelessly and include hardware and software platforms for their operation.

Other aspects of the invention, including assemblies, kits, subassemblies, component parts, methods and processes of making and using, and the like which constitute part of the invention, will become more apparent upon reading the following detailed description of the exemplary embodiments.

DETAIL DESCRIPTION OF A PREFERRED EMBODIMENT(S)

Figure 1A:
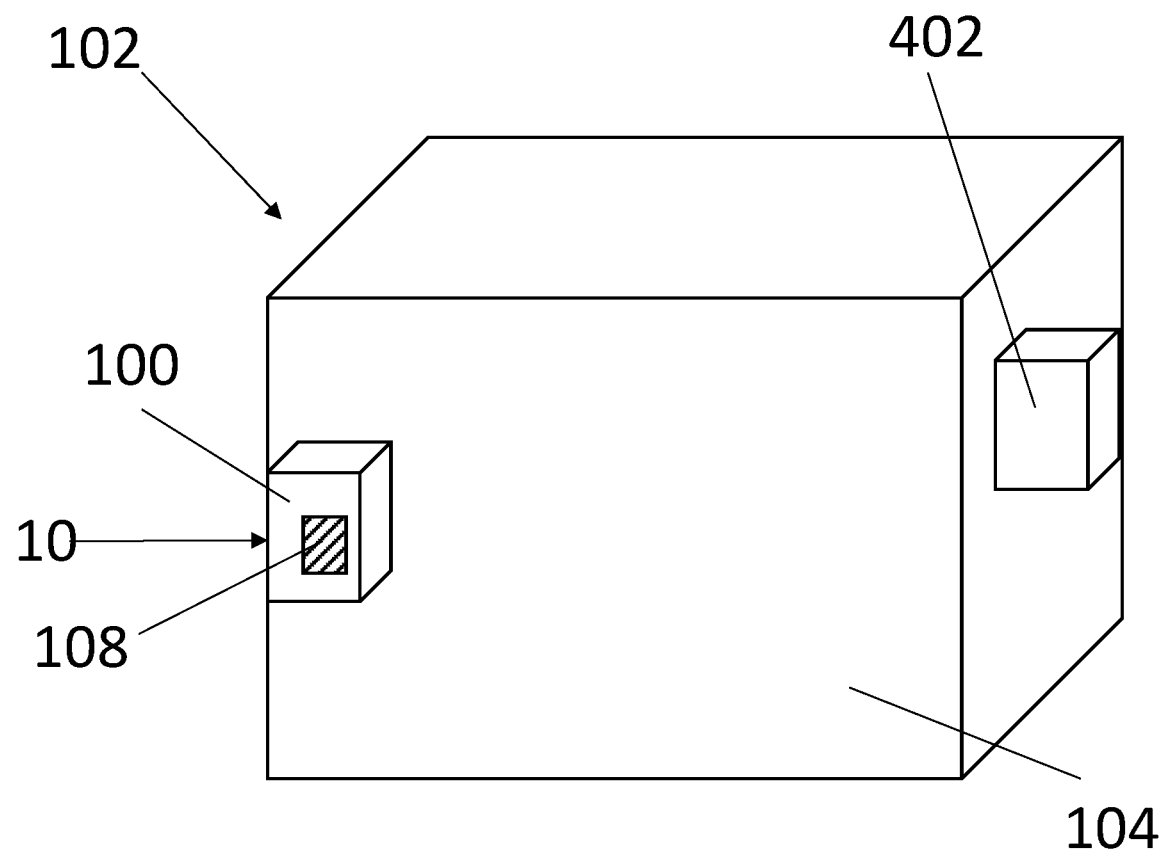
FIGS. 1A and 1B shows a perspective view and a top view, respectively, of a container having a sensor assembly and an output device attached thereto.
Figure 1B:
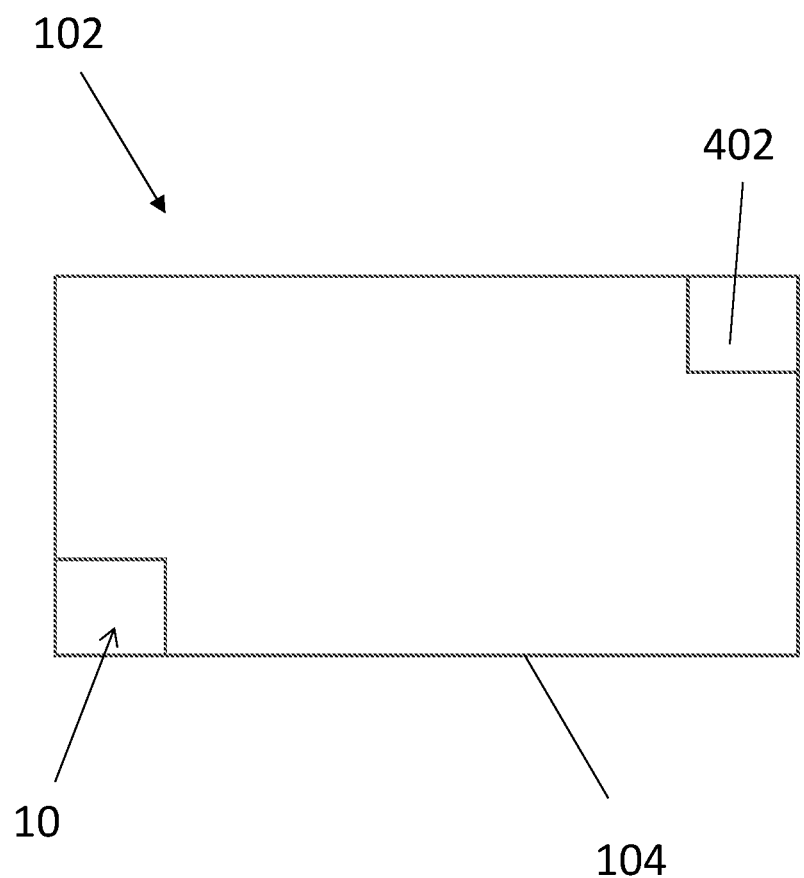
Figure 2:
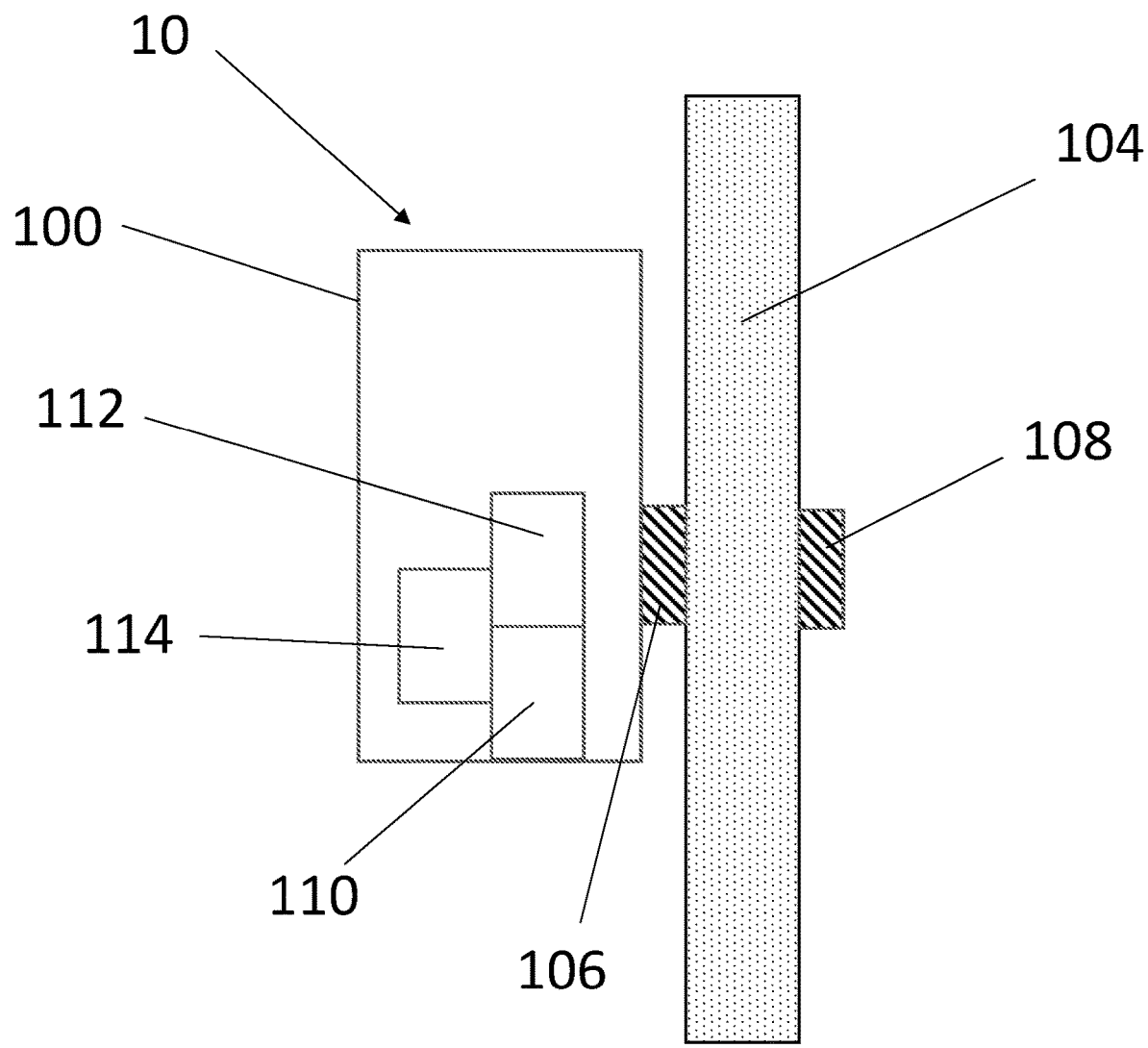
FIG. 2 shows a partial side view of a container wall having a sensor assembly housing attached thereto with two magnets.
Figure 3:
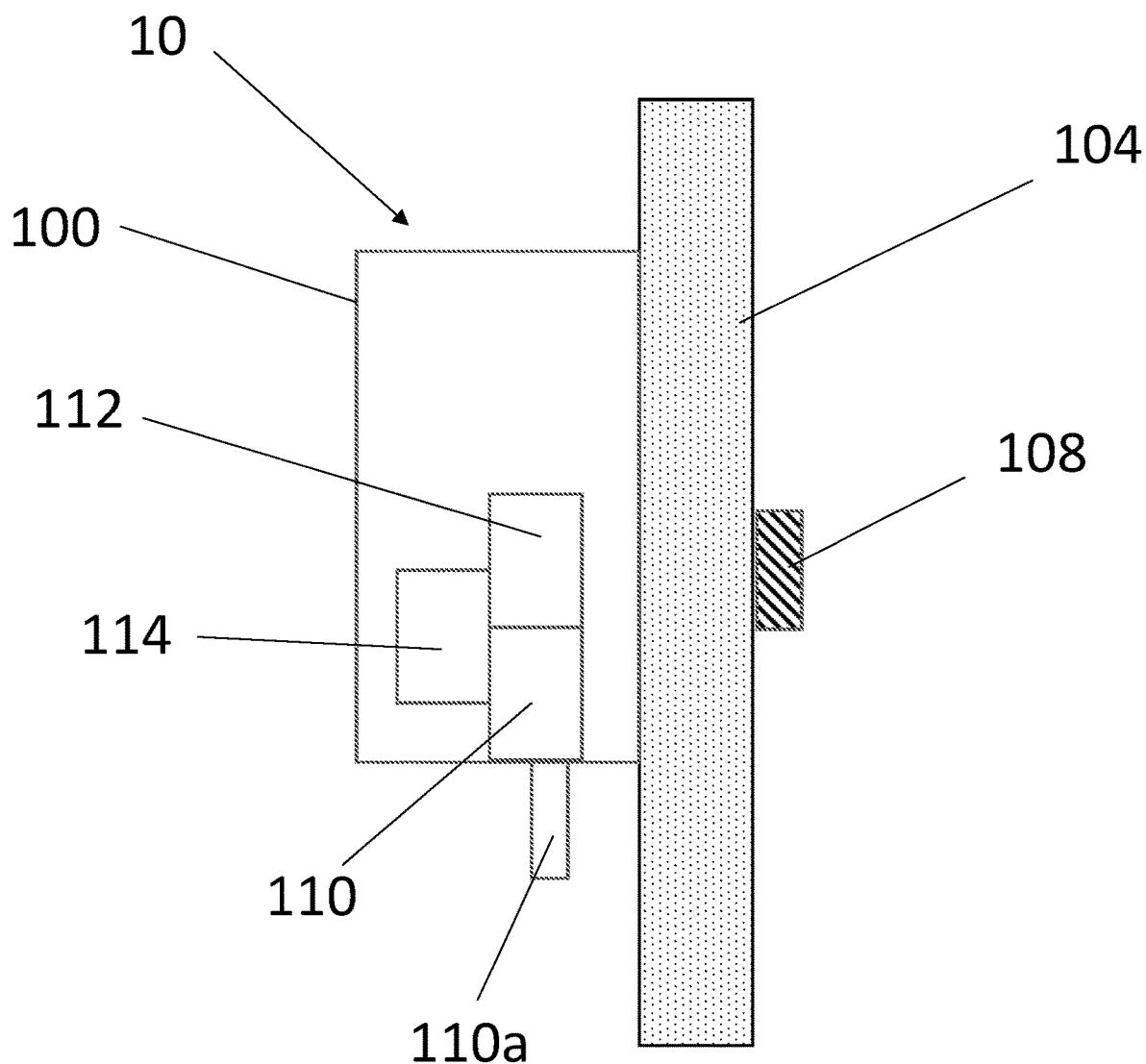
FIG. 3 shows a partial side view of a container wall having a sensor assembly housing attached thereto with one magnet on the outside of the container.

One or more sensor assemblies 10 and cooperating systems are used to monitor conditions of a container, such as of an aquarium, vivarium, terrarium or like habitat. A sensor that is part of the sensor assembly 10 measures conditions within the container, such as temperature, conductivity, pH, oxygen reduction potential, liquid level, turbidity, humidity, or combinations thereof. The measurement allows a user to be apprised of the conditions within the container and/or to optimize the conditions within the container through use of an associated output device, such as a heater. Referring to FIGS. 1A and 1B, the sensor is contained in a housing 100 that is attached to a wall 104 of a container 102. Preferably, the housing 100 is magnetically attached to the wall 104. For example, the housing may contain a magnet 106 on its surface (FIG. 2). To attach the housing 100 to the inside of the wall 104, a second magnet 108 is placed on the outside of the wall 104. The magnetic attraction between the magnets 106,108 holds the housing 100 to the inside of the wall 104 (FIG. 2) within the environment to be monitored. The wall 104 may be made of glass or transparent polymer of the sort used to manufacture an aquarium, for example. The magnetic attraction between the magnets 106, 108 is of sufficient strength to hold and maintain the housing 100 to the wall 104 in a position determined by the user. Alternatively, the housing 100 may be constructed of a magnetic material, provided that the sensor is shielded from magnetic attraction. In that case, only the second magnet 108 is needed on the outside of the wall 104, to hold the housing 100 to the wall 104 (FIG. 3). Depending on the sensor contained within the housing 100, the housing 100 may be completely or partially submerged in water, e.g., if the container 102 is an aquarium, for example. The housing 100 is preferably located within the container 102 at a location that is appropriate for measuring attribute(s) to be measured.

Referring to FIG. 2, the sensor assembly 10 preferably includes the housing 100 containing a sensor 110, a transmitter 112 operably connected to the sensor 110, and a power source 114 for powering the sensor 110. The sensor 110 may measure, but is not limited to, temperature, conductivity, pH, oxygen reduction potential, liquid level, turbidity, humidity, luminous intensity, luminous chromaticity, or combinations thereof. Some specific sensors are show in Table 1 below. The sensor 110 may be entirely contained within the housing 100 or may have portions protruding from the housing 100 as may be necessary for accurate measurement. For example, if the sensor must be in direct contact with water or air in the container 102, such as for measuring pH or conductivity, then a portion of the sensor 110 must be in contact with the water or air and thus may be positioned to protrude from the housing 100 for a proper measurement to be taken. For example, FIG. 3 shows a portion 110a of the sensor 110 protruding from the housing 100. In that event, an appropriate seal is interposed between the housing 100 and the portion of the sensor 110 protruding from the housing 100 in order to avoid damage to the electrical/electronic components within the housing 100. The sensor 110 may be obtained from one or more companies that design and manufacture sensors. A comprehensive list of sensor companies can be found at sites of industry groups, such as the MEMS & Sensors Industry Group, online industry directories, such as www.sensorsportal.com and www.sens2b-sensors.com, or through industry events, such as the annual Sensor Expo.

TABLE 1

| Measurement | Sensor | | | |
|---|---|---|---|---|
| Temperature | Thermistor | Thermocouple | | |
| Humidity | Capacitive | Resistive | Thermal conductivity | Absorption spectroscopy |
| Water moisture | Resistive | Impedance | Near infrared reflectance | |
| Water level | Hall effect | Capacitive | Photo interrupter | |
| Light | Photodiode | Phototransistor | | |

The transmitter 112 is electronically connected to the sensor 110 and is configured to transmit the measurements made by the sensor 110 to a wireless network as described below. Preferably, the transmitter 112 is a radio transmitting at a frequency set by a network configured to receive the measurement. The information from the sensor 110 may be used to control an output device associated with the sensor 110. For example, temperature measurements from a temperature sensor may be used to control a heater and/or a water cooler, such as an electric resistance heater, in the container 102; humidity measurements from a humidity sensor may be used to control a humidifier in the container 102; water level measurements may be used to control a water pump to pump water into or out of the container 102; and pH measurement may be used to control a pump for adding acid or base to the container 102.

The sensor 110 (via the transmitter 112) preferably communicates wirelessly with a user interface 400 (see FIG. 4B), such as resident on a computer, a tablet, a mobile phone, etc. Preferably, the sensor assembly 10 communicates with the user interface electronically (i.e., transmits the measurement from the sensor 110) through electronic communication devices that may include other sensors, gateways, switches, routers, hubs, or any other electronic communication device to computer servers that are located remotely. The sensor assembly 10 may transmit its measurements on an ongoing basis or intermittently (preferably intermittently), directly to the user interface or via the other electronic communication devices. The communication preferably uses wireless technologies and protocols for electronic communication such as cellular (3G/4G/5G), Bluetooth, Bluetooth Low Energy, Wi-Fi, TCP/IP, IEEE 802.15.4 mesh, and other such technologies and protocols. Preferably, Bluetooth technology and/or IEEE 802.15.4 mesh are used for communication.

Figure 4A:
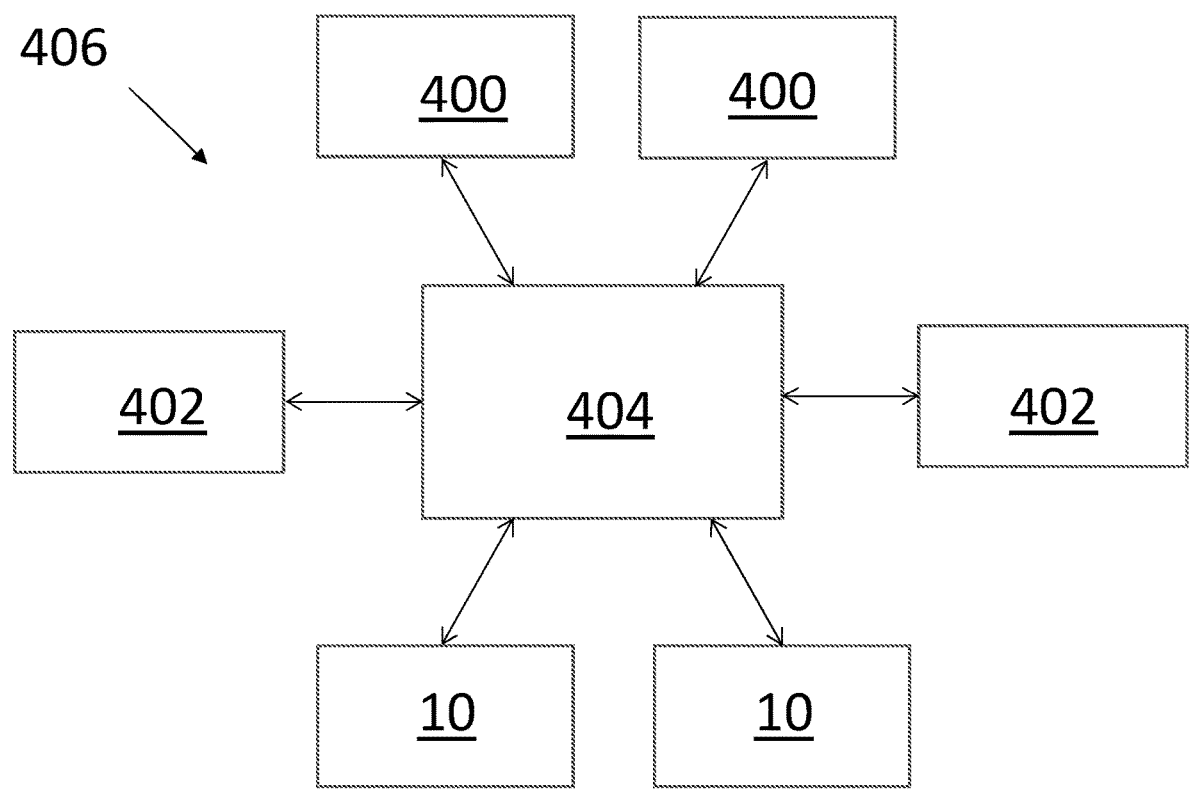
FIGS. 4A and 4B are diagrams showing communication networks of the system of the present invention.
Figure 4B:
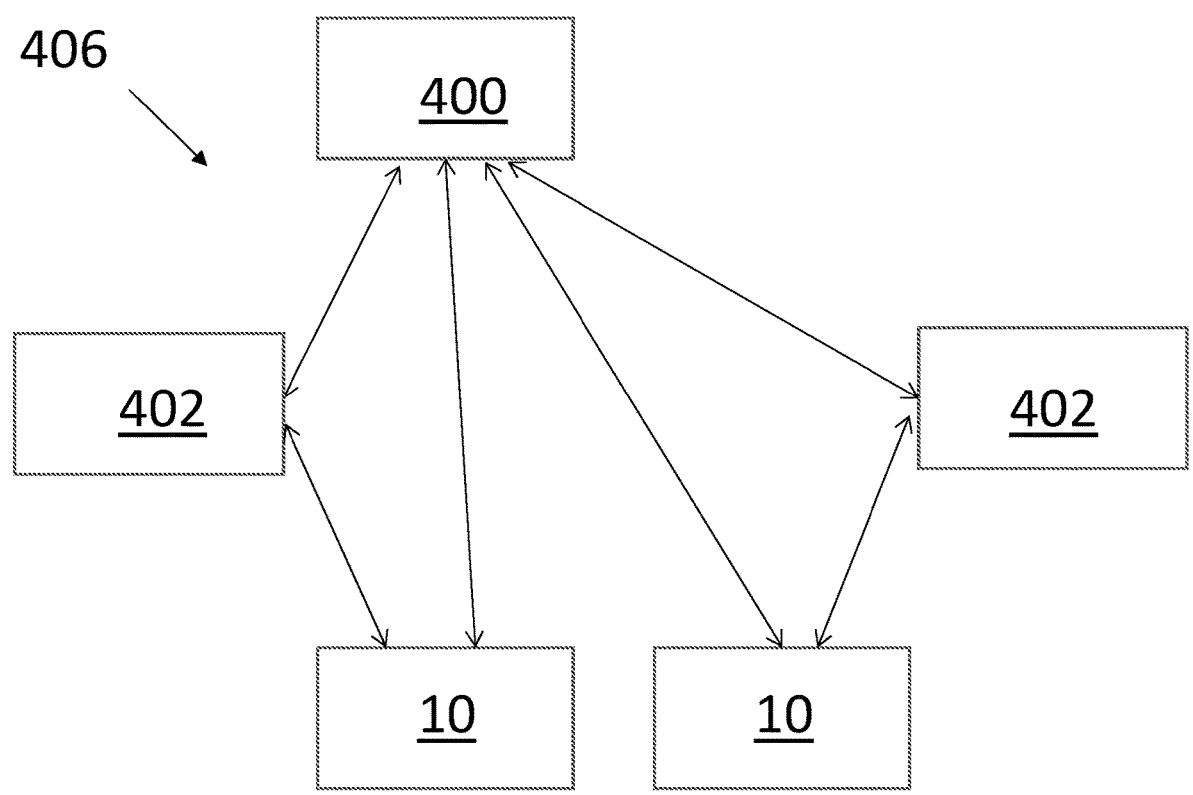

In certain embodiments, as shown in FIG. 4A, the sensor assembly 10, its associated output device 402 and/or one or more user interfaces 400 communicates with a main system 404. The output device 402 receives the measurement from the sensor assembly 10 and controls the quantity measured by the sensor assembly 10. For example, the sensor assembly 10 can measure temperature and the output device 402 is a heater for controlling the temperature. The main system 404 may be a server or a cloud-based system containing software and hardware platforms for communicating, controlling, and recording data within the network 406. The main system provides storage for long term data (so that the user can track the system operation), and a communication pathway for a user to interact with the output device 402 and/or the sensor assembly 10 when he/she is outside of Bluetooth range. Preferably the main system is a cloud system to allow communication over the Internet to the output device 402 and/or the sensor assembly 10. At the same time, as shown in FIG. 4B, each user interface 400, sensor assembly 10, and its associated output device 402 can communicate directly with each other, via lower power wireless area network, such as, Bluetooth Low Energy (BLE) or IEEE 802.15.4 mesh.

The sensor assembly 10, the output device 402, the user interface 400, and the main system 404 form a network 406 which is provided with a hardware and software platform for communication and control of the output device 402. Preferably, the output device 402, sensor assembly 10, and user interface 400 communicate with the main system 404 via wireless technologies and protocols for electronic communication such as cellular (3G/4G/5G), Bluetooth, Bluetooth Low Energy, Wi-Fi, TCP/IP, near field communication (NFC), and other such technologies and protocols. Preferably, Bluetooth technology and/or IEEE 802.15.4 mesh are used for communication. Preferably, communication between the output device 402, the sensor assembly 10, the user interface 400, and the main system 404 is encrypted to ensure security.

The power source 114 preferably is a battery. To conserve battery power, the sensor assembly 10 preferably functions as an "end device" in a network. An "end device" does not act as relays or routers of network traffic from one product to another, but merely sends its signal to the network. Preferably, the sensor assembly 10 is a "sleepy" device, meaning that it operates at a duty cycle sufficient to be effective for the application, but also to maximize battery life by placing the microprocessors into low-power modes optimized for the particular application. For example, the sensor assembly 10 does not operate continuously, but only wakes up periodically to measure and/or send its measurement. Moreover, the sensor 110 and the transmitter 112 need not be powered simultaneously. The transmitter 112 may be powered only when transmission of a measurement is needed, e.g., when the measurement is outside of a preset range or when transmission of the measurement is requested (see, e.g., below, when a measurement is requested from the output device). In these states, the circuitry can be in a state considered active but with current draw at a minimum, preferably in the hundreds of nano-amps range. The frequency at which the sensor 110 and/or the transmitter 112 wake up may be adjusted by the user or based on the sensing method and hysteresis, if any, of the macro-system that assembly is measuring.

Thus, in general the sensor assembly 10 will only transmit measurement data to the output device 402 when the measurement falls outside the preset range, but in the event that the parameter being measured stays within the preset range for a long period of time, the output device 402 may directly ask for a current measurement value from the sensor assembly 10 as a means to make sure that the sensor assembly 10 is still operating properly. Not hearing data from the sensor assembly 10 could mean that the parameter being measured is perfectly within range, but it could also mean that the sensor assembly 10 is not functioning properly or has stopped working altogether. The ability for the output device 402 to query the sensor assembly 10 directly is important to periodically validate the correct functionality of the sensor assembly 10. Preferably, if the output device 402 does not receive a measurement from the sensor assembly 10 for at least 30 minutes, the output device 402 sends a query to the sensor assembly 10 for a measurement. However, that timing may vary depending on the particular sensor assembly 10 and output device 402 involved, and adjustment of the timing is within the ability of a skilled person in the art given the disclosure herein.

In an exemplary temperature sensor assembly, the housing 100 contains a battery, a radio, and a temperature sensor. The housing 100 may be attached magnetically to a wall of the container or may freely float in water contained in the container. A temperature sensor assembly is preferably programmed with a temperature or temperature range the user wishes to maintain. There preferably is another device on the network that can act if the temperature is too low, such as a heater if the temperature is below the desired temperature, or if the temperature is too high, such as a chiller.

The sensor assembly 10 during regular operation may "power up" periodically, e.g., every 100 milliseconds, to measure the temperature. If the measurement is within the user specified range of temperature, the sensor assembly 10 goes back to a low-power mode without powering up the radio for transmitting the measured value. Only when the temperature is outside of the user specified range is the radio powered to send the temperature measurement to the network. On a longer timescale, e.g., every minute, regardless of the measured value, the sensor assembly 10 fully powers on to measure and transmit the temperature or other attribute being measured. The duty cycle or frequency of full power up may be dynamic and based upon the activity of the system or preset by the user.

Figure 5:
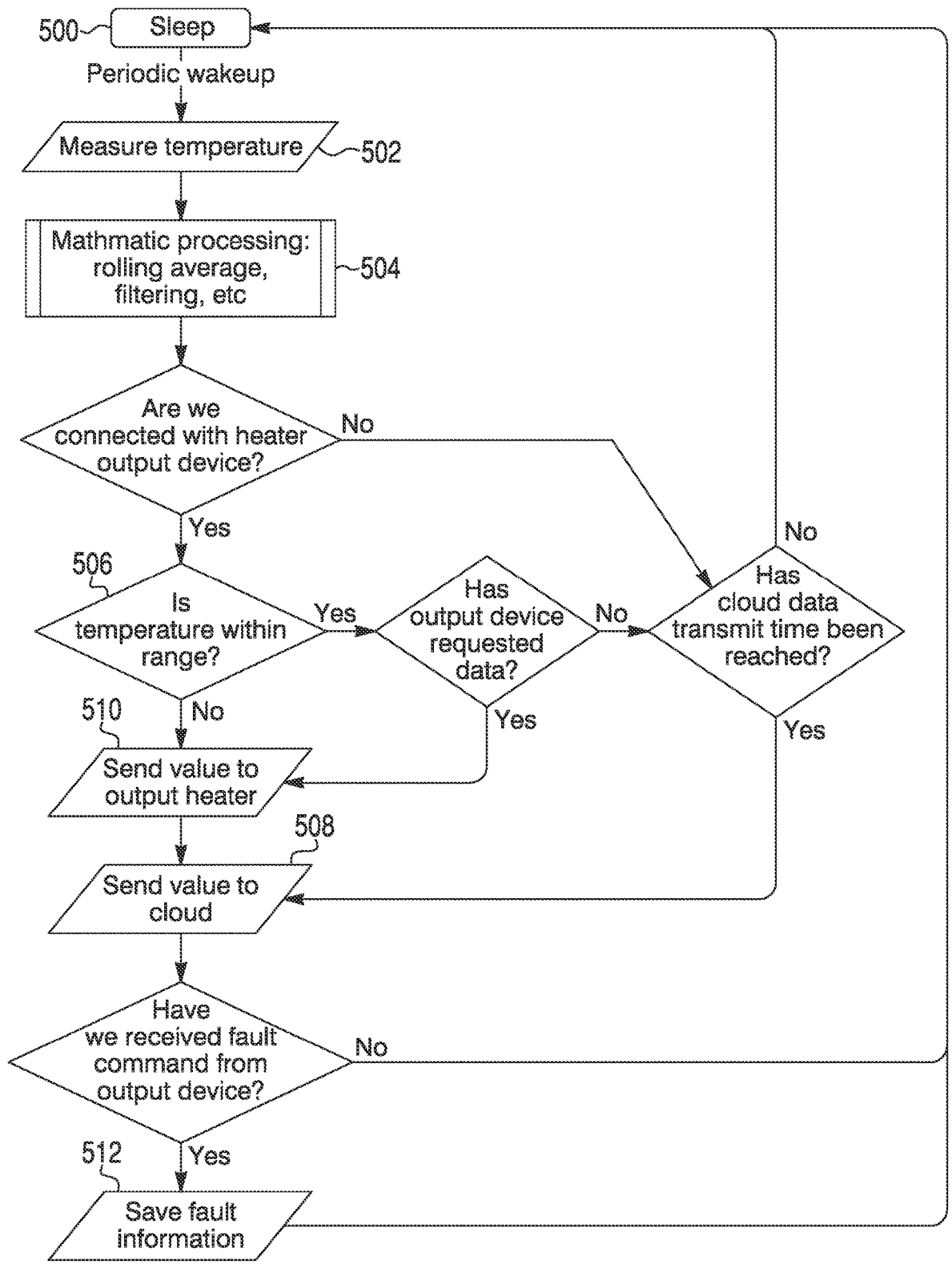
FIG. 5 is a flow diagram for a temperature sensor operation.

FIG. 5 is a chart diagram showing the operation of a temperature sensor. The temperature sensor is periodically activated from sleep mode (box 500) to take temperature measurements (box 502). For the temperature sensor, the sensor preferably sleeps for 1 second before waking up to sample the temperature, and it then goes to sleep for another 1 second. When taking a temperature measurement, it is preferred that multiple individual measurements are taken over a period of time. Preferably, at least three (3) measurements are taken back-to-back and averaged (box 504). In certain embodiments, an outlier measurement, such as highest and/or lowest measurement, is discarded and not included in the averaged value. All measurements should be within a certain allowable range based on the accuracy of the sensor, surrounding hardware and the analog to digital converter. If one or more of the measurements is beyond the acceptable range, then the sensor can recognize that there is some form of unacceptable error and eliminate the error measurement. If only one measurement is taken, then that value is just accepted as valid. If more than one measurement is taken, the result provides an average that is more accurate than a single measurement.

If the temperature sensor is connected to a heater, the sensor checks if the measured temperature is within a preset range (box 506) as set by the user (see description of FIG. 6 below). If the temperature sensor is not connected to a heater, then the temperature sensor goes back to sleep (box 500) or sends the measured temperature value to be saved on the main system 404 (box 508). In certain embodiments, some users only want to observe the temperature over time, but are not controlling the temperature. In that case, the temperature sensor is not connected to the heater. If the measured temperature is not within the preset range, it is sent to the heater for temperature control (box 510) and sent to the main system 404 to be recorded (box 508). If an error is detected in the heater (see below for description of FIG. 6) and communicated to the temperature sensor, the fault information is recorded on the main system 404 (box 512). Preferably, the main system 404 communicates the error to the user interface 400 to alert the user of the error. The temperature sensor then goes back to sleep as noted above to maximize battery life.

Figure 6:
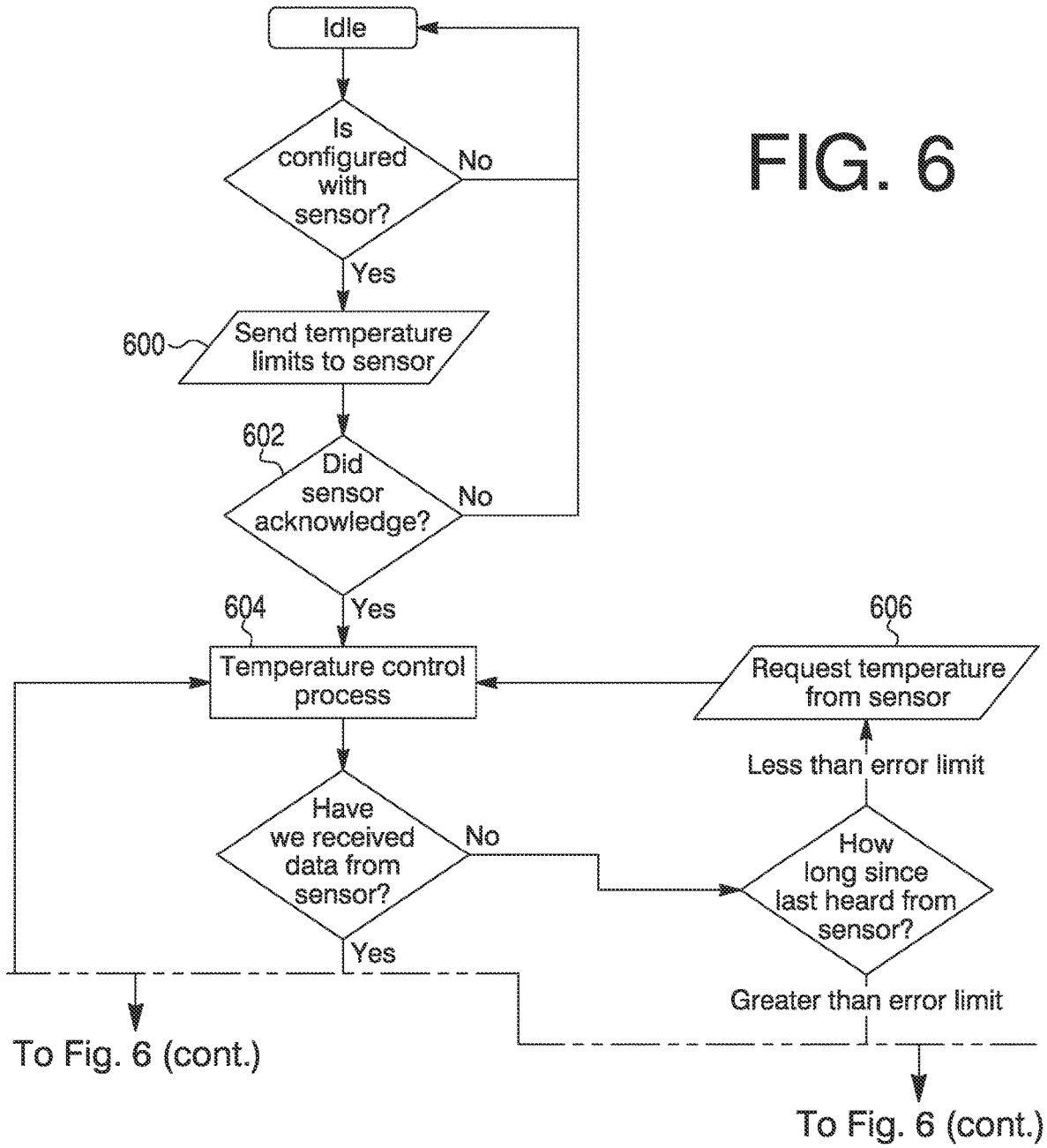
FIG. 6 is a flow diagram for a heater operation.
Figure 6:
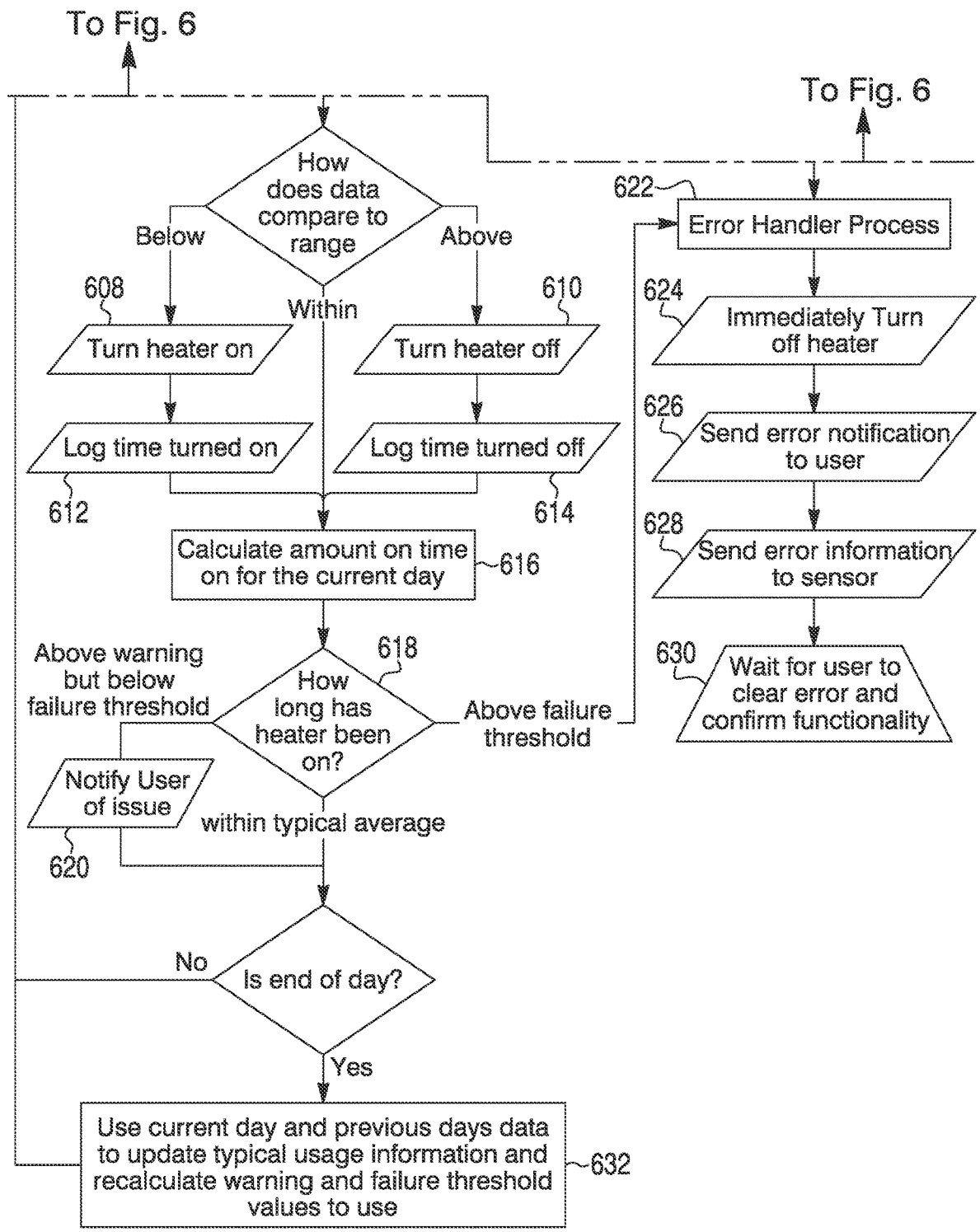

FIG. 6 is a chart diagram showing the operation of a heater in communication with a temperature sensor, such as the sensor of FIG. 5. The heater is preferably an electric resistance heater configured to heat the water when the temperature measurement of the temperature sensor is below the preset range to keep the temperature of the water within that range. That temperature range is preferably set by the user directly on the heater or via his/her user interface 400. This temperature range is sent to the temperature sensor by the heater (box 600), so that the temperature sensor can compare its measurement with the range (box 506). Once the temperature sensor acknowledges receipt of the temperature range (box 602), temperature control by the heater cooperating with the sensor commences (box 604). The heater may automatically receive the temperature measurement from the temperature sensor, e.g., when the temperature sensor periodically measures the temperature, or may request a temperature measurement from the sensor (box 606). As noted above, if the heater does not hear from the temperature sensor in a predetermined period of time, such could indicate a malfunction of the temperature sensor. As such, preferably, if the heater does not hear from the temperature sensor in 30 continuous minutes, the heater will request a measurement from the temperature sensor to ensure that the temperature sensor is still functioning.

Once the temperature reading is received by the heater, the heater is turned on if the reading is below the set range (box 608), or off if the reading is above the set range (box 610). The durations for the heater to stay on and off are logged to keep track of the amount of time in a day required to keep the temperature within the preset range (boxes 612 and 614). For example, to keep the temperature within the range, the heater may typically need to be on for 8 hours and off for 16 hours of the day. This amount of on time is logged daily and averaged to determine an average time required to keep the aquarium or vivarium within the preset temperature range. Preferably, the amount of on time is averaged over thirty (30) days. Since seasonal changes affect the amount of time per day the heater is running, i.e., longer in January than July, during the seasonal change period, it is possible that only recent data, e.g., the last week average, rather than the 30-day average is used for this purpose. The averaging during seasonal changes may be programmed on to the heater at manufacturing. If a temperature reading is within the range or brought into the range by the heater, the heater then calculates the amount of time the heater has been on for the day (box 616). This amount of time is then compared to the average time (box 618) for a given day during the running 30-day period. If the amount of time is above the average time, but less than a maximum daily operating time (failure threshold), the user is notified of the irregularity (the amount of time is above the average time) via the user interfaces 400 (box 620). Preferably, the heater is programmed to trigger an irregularity notification at least one standard deviation above the average time. The failure threshold is preferably set at two standard deviation above the average amount of time. If the amount of time is above the failure threshold, an error handler is activated (box 622), which immediately turns off the heater (box 624), sends an error message to the user via the user interface 400 (box 626) and to the temperature sensor (box 628), and waits for the user to clear the error and confirm proper functioning of the heater (box 630). The user may clear the error directly on the heater or through the user interface 400. At the end of the day, the amount of time the heater has been on for the day is then averaged with the existing averaged time to be used for the next day (box 632).

Figure 7:
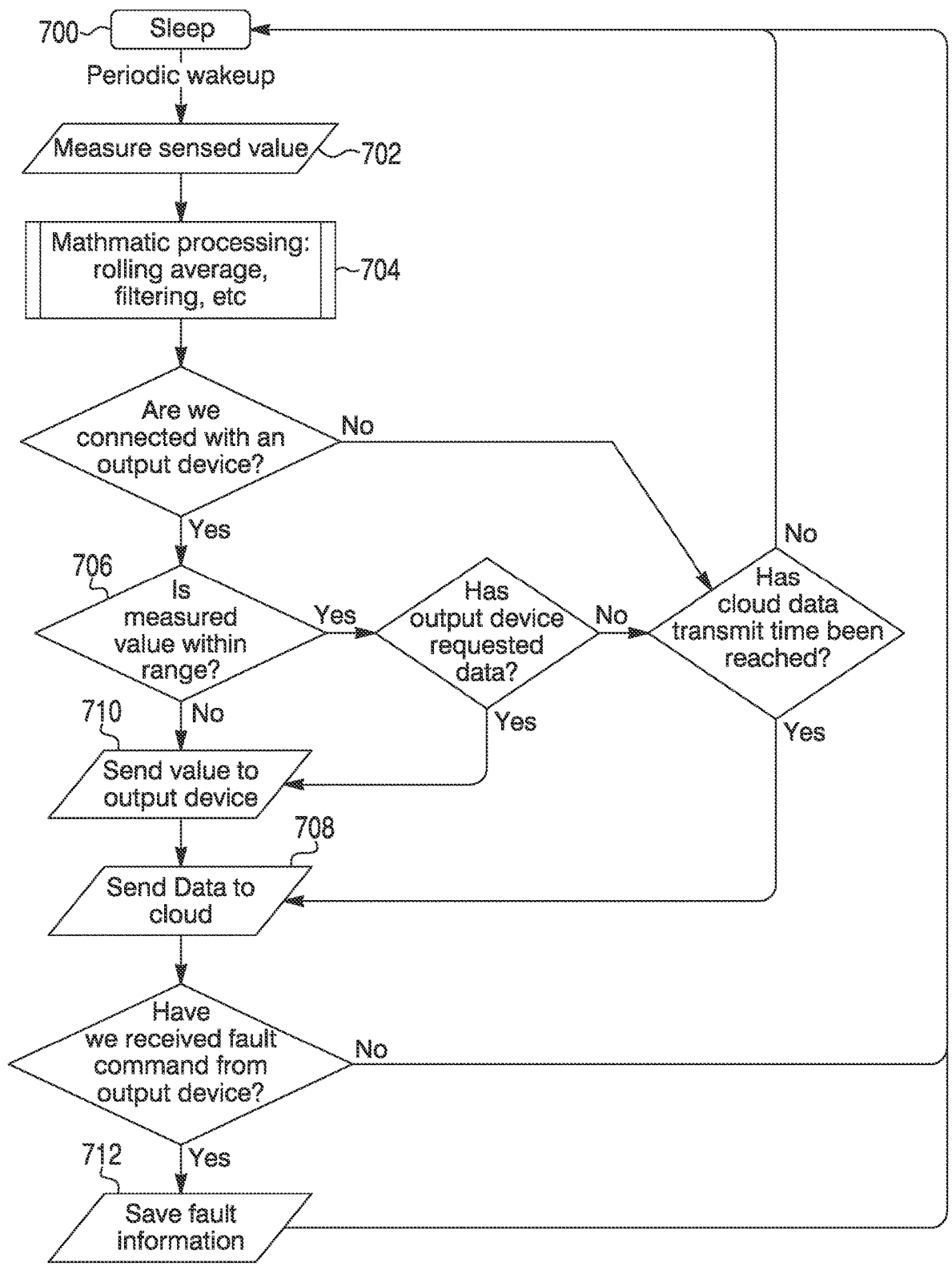
FIG. 7 is a flow diagram for a generic sensor assembly operation.
Figure 8:
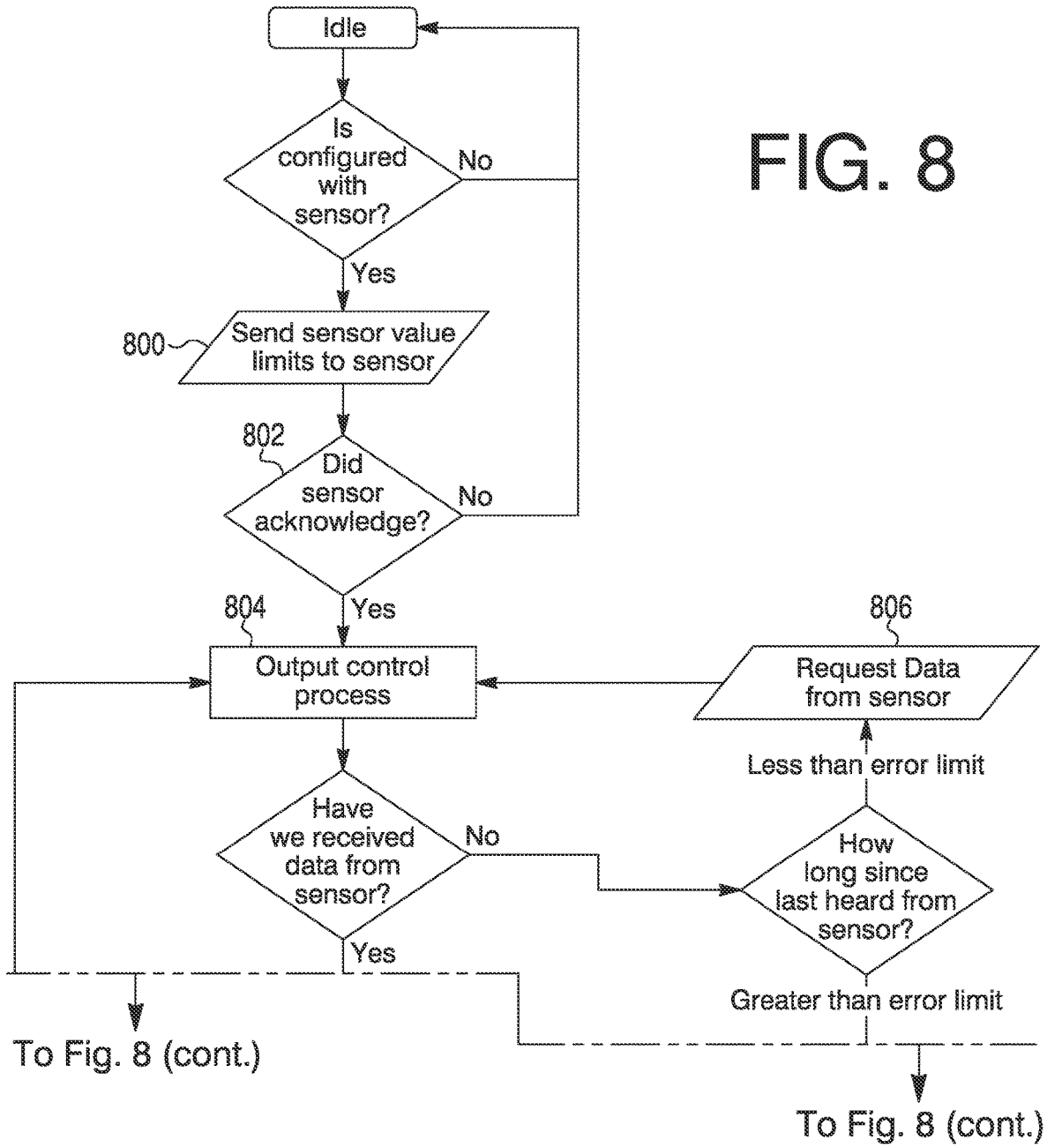
FIG. 8 is a flow diagram for a generic output device operation.
Figure 8:
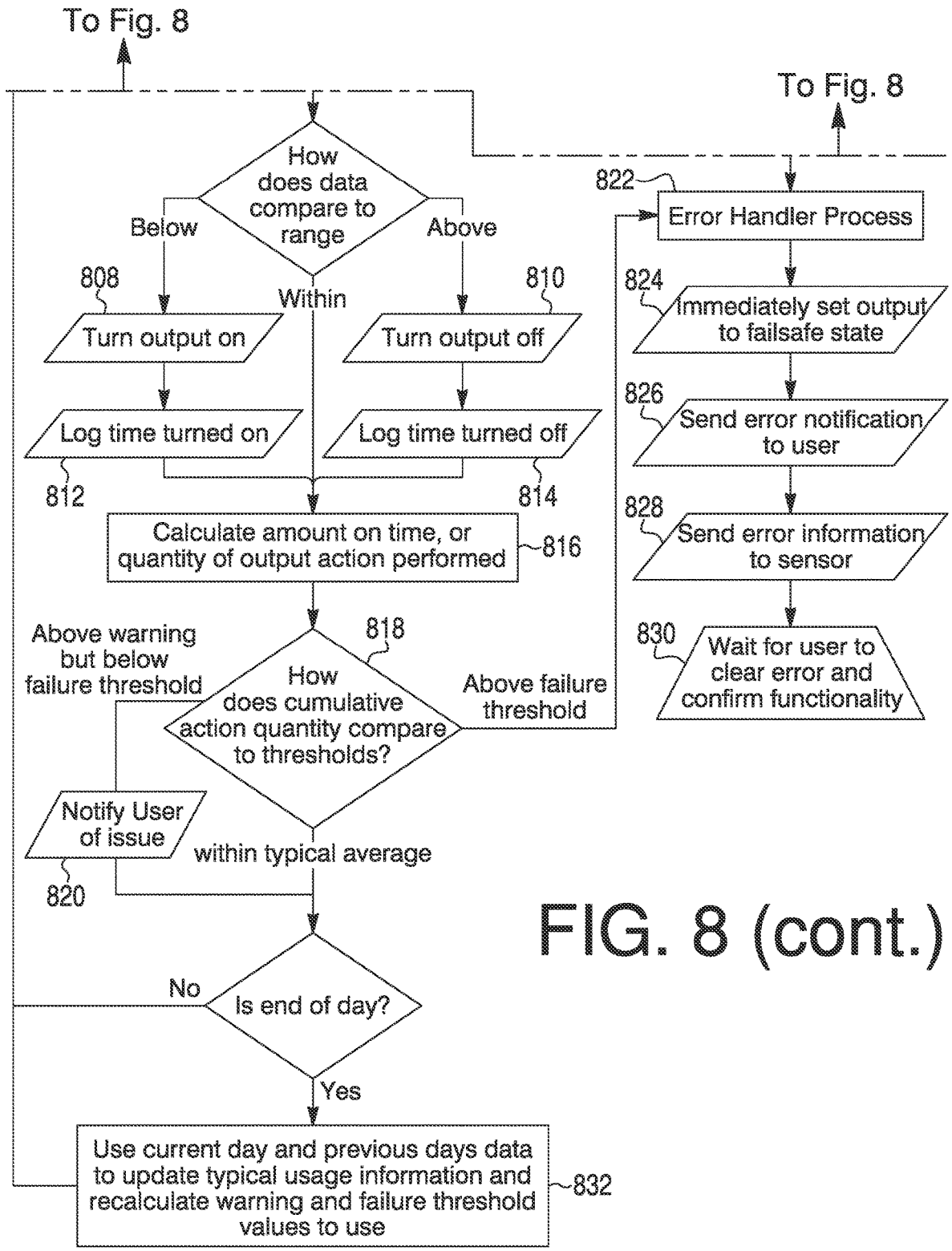

FIGS. 7-8 shows generalized flow charts for a generic sensor assembly 10 and associated output device 402, respectively, which can be operated similarly to the temperature sensor and heater (output device) described above. Referring to FIG. 7, the sensor assembly 10 is periodically activated from sleep mode (box 700) to take measurements (box 702). The amount of time the sensor assembly 10 sleeps and how often it wakes is a balance between conserving battery power and ability to quickly react to changes in the parameter being measured; therefore, each sensor type will have a different sleep time and wakeup period. A skilled person in the art would be able to program the sensor assembly 402 for measurements based on battery power conception and the parameter being measured. Several factors should be considered when determining the sleep time and wakeup period for a sensor assembly 10, including the amount of power the sensor assembly 10 consumes while taking a measurement (e.g., the amount of power the thermistor or hall effect sensor consume while it is actively measuring its value), and the amount of time the sensor assembly 10 needs to be powered to obtain an accurate measurement (e.g., a resistive thermistor does not need to be powered very long to measure its resistance to give a temperature, but a capacitive water level sensor requires charging and discharging, or measuring of frequency change of an applied signal to obtain a capacitance value, which takes much longer, and thus more power; some integrated circuit MEMs sensors also have warm up times that must occur before a measurement occurs). Those two parameters define how much energy is consumed while taking a measurement. On top of energy consumption, the frequency of measurement also adds to the overall amount of energy consumed by the sensor assembly 10 over time. The frequency of measurement, which can also be defined as measurement sampling period (time between measurements, is preferably selected based on how quickly the parameter being measured changes over time. When taking a measurement, it is preferred that multiple individual measurements are taken over a period of time. The sample time and sampling rate are preferably chosen to provide a fast enough response time for the parameter being measured, while balancing with battery longevity. Depending on the parameter being measured, some parameters might need to be sampled every 100 ms, while some parameters might only need to be sampled every minute or more. For example, water temperature is a slow changing parameter in an aquarium due to the high thermal capacity of water, i.e., the water temperature changes slowly over time. Because of that, water temperature does not need to be sampled very often, once per minute is sufficient to determine accurate temperature changes within an aquarium. On the other hand, water level in an aquarium, if the aquarium is small and the pump adding water is fast, can change quickly; therefore, while water is being added into the aquarium, sampling every second is warranted in order to detect fast changes in water level. Adjustment of the sample time and sampling rate depend on the parameter being measured and are within the ability of a skilled person in the art given the disclosure herein. Those individual measurements are then processed, e.g., averaged or filtered, to a single value (box 704). Preferably, at least three (3) measurements are taken back-to-back during a sampling period and averaged. In certain embodiments, the outlier measurements, such as highest and/or lowest measurement, are discarded and not included in the averaged value.

All measurements should be within a certain allowable range based on the accuracy of the sensor and surrounding hardware. If one or more of the measurements is beyond the acceptable range, then the sensor recognizes that there is some form of unacceptable error and flags the issue. If only one measurement is taken then that value is accepted as valid. If more than one measurements are taken and averaged, the average value provides a more accurate measurement. If the sensor assembly 10 is connected to the output device 402, the sensor assembly 10 checks if the value is within a preset range (box 706) as set by the user. If the sensor assembly 10 is not connected to an output device 402, then the sensor assembly 10 goes back to sleep (box 700) or sends the measured temperature value to be saved on the main system 404 (box 708). If the value is not within the preset range, it is sent to the output device 402 for controlling the measured quantity within the aquarium or vivarium (box 710), and sent to the main system 404 to be recorded (box 708). If an error is detected in the output device 402 (see below for description of FIG. 8) and communicated to the sensor assembly 10, the fault information is recorded on the main system 404 (box 712). Preferably, the main system 404 communicates the error to the user interface 400 to alert the user of the error. The sensor assembly 10 then goes back to sleep as noted above to maximize battery life.

Referring to FIG. 8, the output device 402 is configured to maintain the measured value within the preset range. That range is preferably set by the user directly on the output device 402 or via his/her user interfaces 400. The range is sent to the sensor assembly 10 by the output device 402 (box 800), so that the sensor assembly 10 can compare its measurement with the range (box 806). Once the sensor assembly 10 acknowledges receipt of the temperature range (box 802), control of the output device 402 commences (box 804). The output device 402 may automatically receive the measurement value from the sensor assembly 10, e.g., when the sensor assembly 10 periodically makes measurements, or may request a measurement from the sensor assembly 10 (box 806). Once the measured value is received by the output device 402, the output device 402 is turned on or off depending on whether the measured value is below the set range (box 808) or above the set range (box 810).

Although the FIG. 8 shows the output device 402 turned on if the measured value is below the set range and off if the measured value is above the set range, the opposite may also be true depending on the specific output device 402. For example, a water level sensor (sensor assembly 10) may be connected with a dosing pump (output device 402) which doses reverse osmosis, deionized (RO-DI) water to top-off the water in the aquarium to compensate for evaporation. If the water level sensor detects a low water level, it transmits that data to the dosing pump. The dosing pump will turn on to start filling the aquarium with water. When the water level rises to its high limit, it will transmit that data to the dosing pump which in turn will stop pumping water into the aquarium.

The durations for the output device 402 to stay on and off are logged to keep track of the amount of time in a day required to keep the temperature or water level, for example, within the preset range (boxes 812 and 814). These amounts of time are logged daily and averaged, preferably over the last thirty (30) days, to determine an average on time required to keep the aquarium or vivarium within the preset range. If the measured value is within the range or brought into the range by the output device 402, the output device 402 then calculates the amount of time the output device 403 has been on for the day (box 816). This amount of time is then compared to the average time stored on the main system (box 818). If the amount of time is at least one deviation above the average time (as programmed on the output device 402), but less than a maximum daily operating time (failure threshold) (as programmed on the output device 402), the output device 402 notifies the user of the irregularity (the amount of time is above the average time) via the user interfaces 400 (box 820). The failure threshold is preferably set at two standard deviation from the average amount of time. If the amount of time is above the failure threshold, an error handler is activated (box 822), which immediately turns off the output device 402 (box 824), sends an error message to the user via the user interface 400 (box 826) and the sensor assembly 10 (box 828), and waits for the user to clear the error and confirm proper functioning of the output device 402 (box 830). The user may clear the error directly on the output device 402 or through the user interface 400. At the end of the day, the amount of time the output device 402 has been on for the day is then averaged with the existing average time to be used for the next day (box 832).

Although certain presently preferred embodiments of the invention have been specifically described herein, it will be apparent to those skilled in the art to which the invention pertains that variations and modifications of the various embodiments shown and described herein may be made without departing from the spirit and scope of the invention.

What is claimed is:

1. A system for monitoring and controlling an environment of an aquarium, vivarium, or terrarium, the system comprising:
   a. a sensor assembly operably associated with the aquarium, vivarium, or terrarium, wherein the sensor assembly is configured to measure an environmental quantity within the aquarium, vivarium, or terrarium;
   b. an output device attached to the aquarium, vivarium, or terrarium, and in communication with the sensor assembly and configured to control the environmental quantity;
   c. a main system for recording data thereto; and
   d. a user interface,
   the sensor assembly comprising a housing containing a sensor, a transmitter electronically connected to the sensor, and a power source for providing power to the sensor and the transmitter,
   the sensor containing hardware and software configured to keep the sensor in an off state and to turn on periodically to take measurements,
   the user interface communicating with the sensor assembly and the output device via the main system, or the user interface communicating directly with the sensor assembly and the output device.

2. The system of claim 1, wherein the user interface is associated with a computer, a tablet, a mobile phone.

3. The system of claim 1, wherein communication between the sensor assembly, the output device, the main system, and the user interface is wireless.

4. The system of claim 1, wherein the sensor assembly, the output device, the main system, and the user interface include hardware and software for communication and control of the output device.

5. The system of claim 1, wherein the sensor assembly comprises a temperature sensor and the output device comprises a heater and/or a water cooler; or the sensor assembly comprises a water level sensor and the output device comprises a water pump; or the sensor assembly comprises a pH sensor and the output device comprises a base additive pump.

6. The system of claim 1, wherein the user interface is configured to provide a preset environmental quantity to maintain within the aquarium, vivarium, or terrarium.

7. The system of claim 1, wherein the sensor is one or more of a temperature sensor, a conductivity sensor, a pH sensor, oxygen reduction potential sensor, a liquid level sensor, at turbidity sensor, a humidity sensor, or combinations thereof.

8. The system of claim 1, wherein the housing has a magnet on a surface thereof for attaching the housing to the aquarium, vivarium, or terrarium.

9. The system of claim 1, wherein the transmitter is turned on only when a measurement is to be transmitted.

10. A method for monitoring and controlling the environment of an aquarium, vivarium, or terrarium, the method comprising the steps of:
    a. providing a sensor assembly comprising a housing containing a sensor, a transmitter electronically connected to the sensor, and a power source for providing power to the sensor and the transmitter;
    b. mounting the sensor assembly and the output device to the aquarium, vivarium, or terrarium;
    c. providing a preset environmental quantity;
    d. measuring the environmental quantity; and
    e. controlling, via the output device, the environmental quantity to be within the preset environmental quantity;
    the sensor containing hardware and software configured to keep the sensor in an off state and to turn on periodically to take measurements.

11. The method of claim 10, wherein the sensor assembly comprises a temperature sensor and the output device comprises a heater; or the sensor assembly comprises a water level sensor and the output device is a water pump; or the sensor assembly comprises a pH sensor and the output device comprises a base additive pump.

12. The method of claim 10, wherein step c is accomplished by entering the present environmental quantity directly on the output device or by the user interface.

13. The method of claim 10, wherein step d involves periodically activating the sensor to measure the environmental quantity.

14. The method of claim 13, wherein the sensor takes several measurements and averages them to provide a single value.

15. The method of claim 14, wherein the value is transmitted to the output device if the value is not within the preset environmental quantity.

16. The method of claim 10, wherein step e involves turning on or off the output device.

17. The method of claim 10, further comprising the step of tracking an amount time during a day when the output device is turned on.

18. The method of claim 17, further comprising the step of comparing the amount of time to an average amount of time the output device is on per day.

19. The method of claim 18, further comprising the step of notifying the user interface when the amount of time is greater than the average amount of time.

* * * * *